United States Patent
Ritsche et al.

[11] Patent Number: 5,938,125
[45] Date of Patent: Aug. 17, 1999

[54] DISCHARGE HEAD FOR MEDIA FOR TREATMENT OF THE THROAT

[75] Inventors: Stefan Ritsche; Esther Amann, both of Radolfzell, Germany

[73] Assignee: Ing. Erich Pfeiffer GmbH, Radolfzell, Germany

[21] Appl. No.: 08/785,029

[22] Filed: Jan. 2, 1997

[30] Foreign Application Priority Data

Jan. 4, 1996 [DE] Germany .............................. 196 00 123

[51] Int. Cl.⁶ ........................................................ B05B 1/00
[52] U.S. Cl. ........................ 239/600; 239/490; 128/200.23
[58] Field of Search ................................. 239/302, 320, 239/321, 322, 337, 375, 463, 468–470, 472, 490, 590, 600; 128/200.14, 200.18, 200.22, 200.23; 604/57, 58, 70, 151

[56] References Cited

U.S. PATENT DOCUMENTS

| | | | |
|---|---|---|---|
| 2,974,880 | 3/1961 | Stewart et al. | 239/493 |
| 3,112,074 | 11/1963 | Green | 239/463 X |
| 3,116,856 | 1/1964 | Prussin et al. | 128/200.23 X |
| 3,129,893 | 4/1964 | Green | 239/337 X |
| 3,648,932 | 3/1972 | Ewald et al. | 239/337 |
| 3,913,842 | 10/1975 | Singer | 239/337 |
| 3,961,756 | 6/1976 | Martini | 239/463 X |
| 3,990,639 | 11/1976 | Laauwe | 239/492 |
| 4,396,152 | 8/1983 | Abplanalp | 239/337 |
| 4,801,093 | 1/1989 | Brunet et al. | 239/490 |
| 5,121,883 | 6/1992 | Jouillat et al. | 239/490 |

FOREIGN PATENT DOCUMENTS

| | | |
|---|---|---|
| 249255 | 9/1966 | Australia . |
| 330951 | 7/1976 | Australia . |
| 0 534 088 A1 | 3/1993 | European Pat. Off. . |
| 1409379 | 7/1965 | France . |
| 2 070 630 | 9/1971 | France . |
| 2360031 | 2/1981 | France . |
| 872 480 | 2/1953 | Germany . |
| 2301520 | 7/1973 | Germany . |
| 86 10 083 | 2/1987 | Germany . |
| 28 26 784 C2 | 10/1988 | Germany . |
| 41 19 132 A1 | 12/1992 | Germany . |
| 43 25 177 A1 | 2/1995 | Germany . |
| 44 29 454 A1 | 2/1996 | Germany . |
| 44 31 019 A1 | 3/1996 | Germany . |

OTHER PUBLICATIONS

European Search Report dated Nov. 12, 1997 in Appln. No. 96119492.5.

German search report dated Jul. 31, 1996 in German Appl. No. 196 00 123.4.

*Primary Examiner*—Andres Kashnikow
*Assistant Examiner*—Steven J. Ganey
*Attorney, Agent, or Firm*—Quarles & Brady LLP

[57] ABSTRACT

A throat beak head (1) comprises an actuating press grip (8) having an integral beak (9) and located therein a filler (23) arranged in a mount (24) diametrically passing through the full length of said press grip (8) and fitted in the emerging direction (36) of the medium from the nozzle (10), as a result of which the risk of parts of the beak (9) being expelled due to the delivery pressure and gaining access to the windpipe when using the head (1) is substantially reduced.

27 Claims, 2 Drawing Sheets

DISCHARGE HEAD FOR MEDIA FOR TREATMENT OF THE THROAT

CROSS-REFERENCE TO RELATED APPLICATION

Not applicable

STATEMENT REGARDING FEDERALLY SPONSORED RESEARCH

Not applicable

TECHNICAL FIELD AND BACKGROUND OF THE INVENTION

The invention relates to a discharge head with which fluid, pasty, powderlike or similar flowable media can be discharged through a nozzle orifice, more particularly atomized in a spray cone or the like. Preferably the nozzle orifice is intended to be deeply inserted, for example at least 20, 40 or 50 mm deep into a body cavity, such as the mouth cavity to then enable the medium to be discharged.

The discharge head comprises a head body forming substantially the entirety of its outer surface or a head part located on a centerline, the head part forming the section of the head body which is widest in cross-section through the corresponding centerline or longitudinal axis in each case, e.g. with the outer shell or face end wall of a cap shape. The nozzle orifice is oriented radially outwards transversely or at right angles to the centerline of the head part and may be located in a radially protruding portion of the head part. This discharge portion or discharge protrusion may be formed directly by the cap shell or by a discharge beak protruding beyond the outer circumference of the former roughly by the cited degree of insertion, the free cross-section of said discharge beak amounting to less than 15, 10 or 7 mm and in the free end surface area of which the nozzle orifice may be provided.

The discharge head may form as the actuating head a finger grip for actuating a discharging dispenser, a plunger pump, for example, or a pressurized aerosol container or the like, whereby as a result of the pressure actuation the discharge unit to be held and to be shortened in a single hand supplies the medium from the discharging dispenser under pressure to the nozzle and is swirled in the region thereof by transverse flow so that it is atomized at the nozzle orifice in being released from the discharge head into the open. The nozzle or the atomizing means directly adjacent to the nozzle orifice may be configured as a single part or multi-part. In the case of a multi-part configuration there is a risk that a nozzle part, particularly the nozzle part through which the nozzle orifice passes, releases itself under the dispensing pressure from the remaining discharge head even when it is retained by a snap-lock fitting, by a press-fit or the like.

If this nozzle part is inserted against the discharging direction of the nozzle orifice into its mount or releasably so roughly in the discharging direction without causing a material fracture, it may be expelled by the dispensing pressure and result in a serious health hazard, when employed in a bodily opening, more particularly by gaining access to the trachea of the user. A similar situation applies also to an integral configuration of the nozzle or of the guiding means for the medium or when the nozzle part may become loose partly or fully from the remaining discharge head due to damage by fracture.

This can be avoided by relatively simple means when the nozzle axis and the actuating axis or centerline of the head part are located parallel to each other or in the same axis, since then the discharge port can be formed integrally with the widened head part to be actuated by the fingers and, apart from this, the nozzle core can be inserted in a mount at the upstream end, this mount connecting the medium pressure space of the discharging dispenser directly and linearly to the nozzle. In this mount the nozzle end passage is located, which is usually very narrow, this passage passing from the pressure chamber or the connection of a passage connecting the latter wider by many times, up to the transverse deflection at the inner end of the nozzle passage more or less linearly and/or with a constant flow cross-section.

For numerous applications, more particularly for deep application in openings it is more expedient ergonomically when the nozzle axis is located transversely to the actuating axis or to the axis about which the discharge unit is clasped on being discharged manually or when the nozzle axis or the nozzle is offset to the side differently with respect to this clasping axis. In this case the nozzle, swirler or a nozzle core or filler cannot be fitted through the passage housing located in the actuating or finger-grip axis in the discharging flow direction of the medium or produced as a molding of a plastics material or the like, instead the nozzle part through which the nozzle orifice passes is to be fitted from the outer side of the head body, for example against the discharging direction which results in the risks as cited.

OBJECTS OF THE INVENTION

The invention is based on the object of defining a discharge head or a discharge unit of the kind stated in which the disadvantages of known configurations or of the kind as described are avoided and which, more particularly, is safeguarded against the head parts from being expelled and ejected from the discharge head by the flow energy of the medium.

SUMMARY OF THE INVENTION

In accordance with the invention the nozzle is integrated in the head part or the discharge protrusion so that expelling of the particles or parts of the nozzle is avoided, more particularly, expelling due to failure of a mount for this nozzle part which may release the nozzle part without material fracture. This safeguard may be attained by a positive lock and/or by an integral configuration of the nozzle part with the head part. This positive lock includes expediently at least one abutment effective against movements roughly in the discharging direction which, for example may be formed by a stop on the head part or the head housing acting on the discharge protrusion.

Irrespective of the configuration described it may be of advantage, more particularly for facilitated fabrication or assembly, to provide in a region of the head part remote from the region of the discharge protrusion an access opening, from which e.g. a mold pusher of an injection mold can be extracted following production of the head body or into which a component, such as a nozzle part, may be inserted from without. The access opening does not pass through the connecting member for connecting the discharge head to the plunger unit or the pressure chamber of the discharging dispenser, it instead being located in an axis departing from the axis of this connecting member, for example in the same axis as the nozzle passage.

As a result of this this nozzle passage may be configured constricted in the discharging direction and pass through an inner end surface area which is provided with recessed or protruding guiding surface areas. For usage the access opening is expediently sealed off by a closure, for example a plug pressed or snapped into place, whilst the receiving passage adjoining the access opening up to the nozzle orifice remains open for through-flow of the medium. Expediently this flow path or the complete discharge head is bare of any valves operating as a function of pressure and/or travel.

Preferably a transverse passage passes through the head body completely, this passage forming at one end the nozzle orifice and at the other end a closable access opening an axial passage for the medium adjoining the transverse passage between these ends from which the medium gains access by angular deflection to the transverse passage and from there to the nozzle.

Particularly when the discharge protrusion is configured correspondingly long a locking anchor may engage therein and in the head part such that even when the discharge protrusion breaks away the broken-off part remains locked in place by the anchor with respect to the head part and is unable to release itself from the head part. This anchor may be formed by the nozzle core or the filler which expediently passes through the full length of the corresponding passage and forms a section of the outermost outer surface area of the discharge head. The discharge head may consist only of a single integral component or of only two integral components of a plastics material or the like in each case.

These and further features are evident not only from the claims but also from the description and the drawings, each of the individual features being achieved by themselves or severally in the form of subcombination in one embodiment of the invention and in other fields and may represent advantageous aspects as well as being patentable in their own right, for which protection is sought in the present.

BRIEF DESCRIPTION OF THE DRAWINGS

Example embodiments of the invention are explained in more detail in the following and illustrated in the drawings in which.

DETAILED DESCRIPTION OF THE PREFERRED EMBODIMENTS

Figures 1, 2:
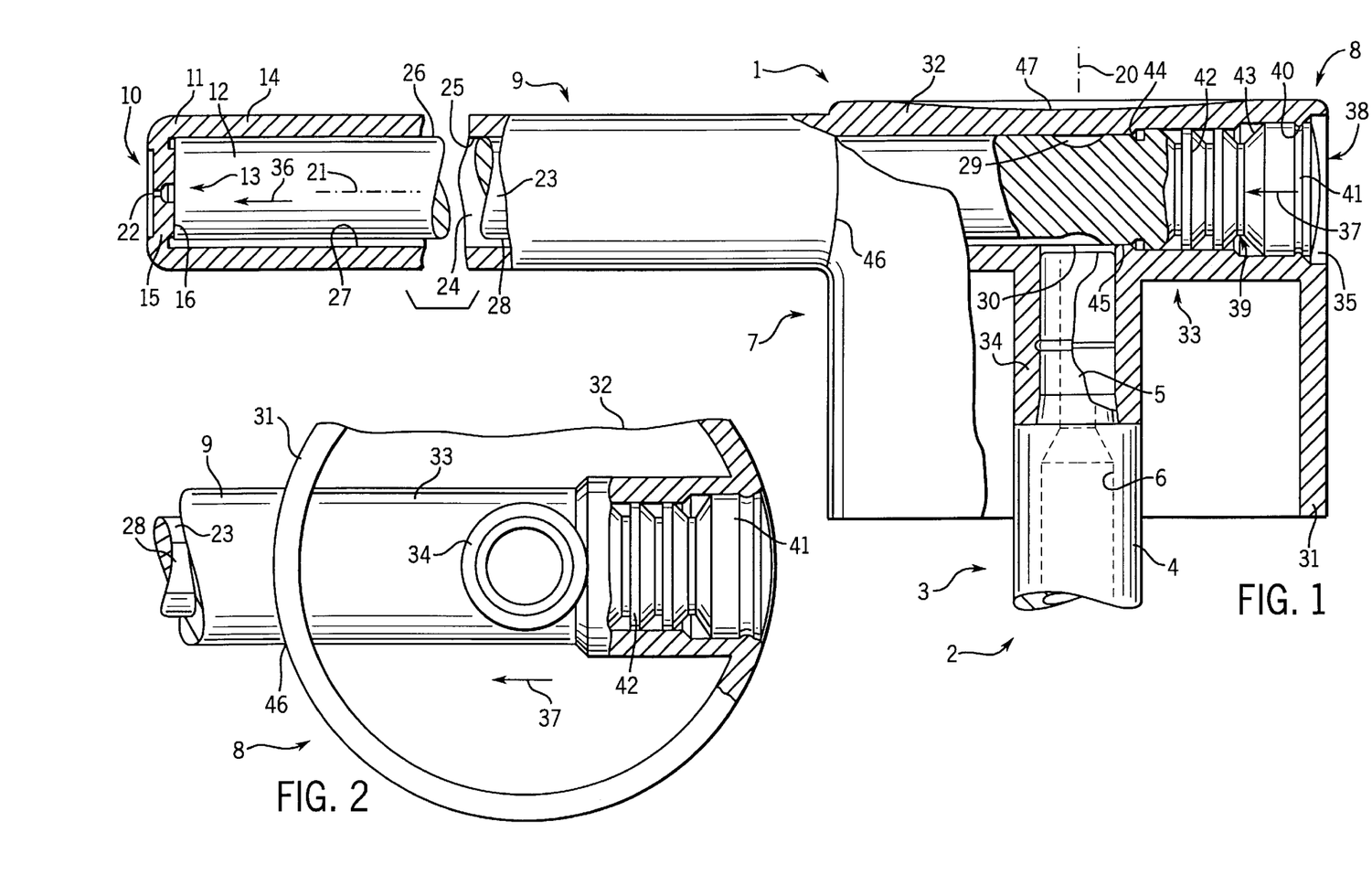
FIG. 1 shows a discharge head according to the invention as viewed partly sectioned.
FIG. 2 shows the discharge head of FIG. 1 as viewed partly sectioned from underneath.
Figure 3:
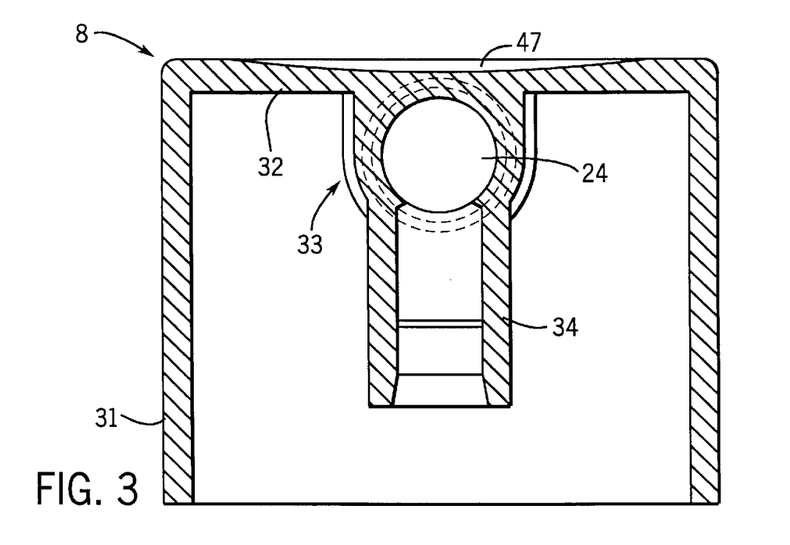
FIG. 3 is a section through the head body of the discharge head.
Figure 4:
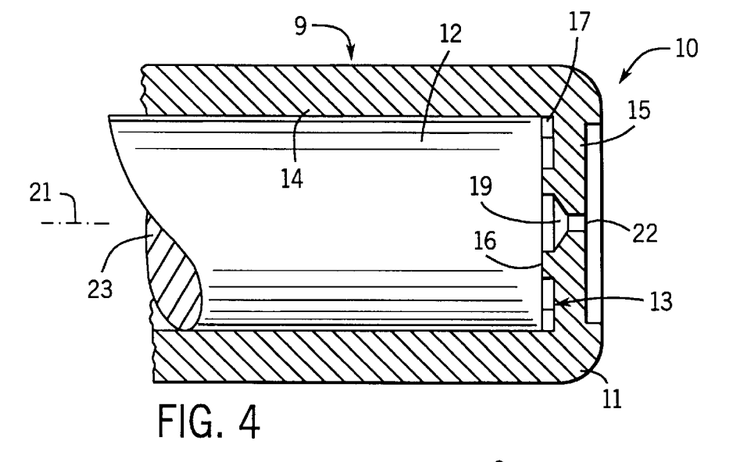
FIG. 4 shows the nozzle portion on a magnified scale and FIG. 5 is a section through the guiding means of the nozzle portion as shown in FIG. 4.
Figure 5:
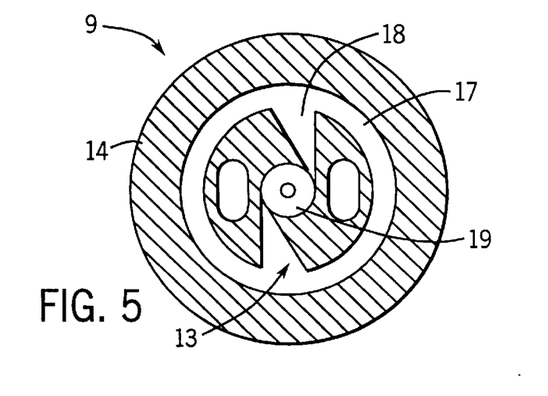

The discharge head 1 serves to actuate a discharging device 2, namely a plunger pump, at the end of which the head 1 is attached as an end piece in the same axis, the pump housing of which it clasps axially. Protruding axially from the pump housing is a actuating unit or plunger unit 3 which carries within the pump housing a plunger piston for constricting and expanding the pressure chamber or pumping chamber by being shifted reciprocatingly and, where necessary, an opening/closing outlet valve. The unit 3 comprises a plunger 4 protruding into the head 1, the free end of which forms a constricted, pin-shaped connecting member 5 for connecting to the head 1. By the unit 3 being pushed into the pump housing the medium gains pressurized access to the pressure chamber, as a result of which the outlet valve opens and the medium flows into the head through a discharge passage 6 in the unit 3. When the head 1 is no longer subjected to the actuating force it reverts to its starting position along with the unit 3 as urged by the return spring, the outlet valve closing and an inlet valve closed during discharge opening so that a further dose of the medium is drawn by the latter from the medium reservoir into the pressure space.

The head 1 consists merely of two integral components made of the same or differing plastics materials, of which the head body 7 serves for directly connecting the counter member 5, whilst the other component has no contact with respect to the dispenser 2 or unit 3 and is located totally submerged within the body 7. The body 7 features a cap-shaped head part 8 directly connected internally to the arrangements 2, 3, this head part being able to clasp the outer and/or inner circumference in each position and in which the counter member 5 is located totally submerged.

Protruding beyond the outer circumference of the cylindrical head part 8 and spaced between the face end surfaces thereof is a discharge member 9 or a protrusion which projects at least two to three times more than the outer width of the head part 8. This outer width is at least three to four times larger than the outer width of the member 9 which serves as a throat beak for introduction into the mouth cavity of the user and which like the head part 8 has an outer shell which is smooth and free of any sharp edges over its full length and an outer width which is constant throughout. The member 9 is located in an axial plane of the head part 8 and at right-angles thereto. The length of the member 9 is at least three to four times more than that of the head part 7, and with respect thereto the length of the other component is even more, namely roughly by the amount of the outer width of the head part 8.

The free end of the member 9 comprises a media nozzle 10 which consists merely of two nozzle parts 11, 12, of which the one may be configured integral with the parts 8, 9 and the other integral with the other component. The cap-shaped nozzle part 11 exposed at its outer circumference and its end integrally adjoins the tubular member 9 and is formed by an end surface area of this tube having a continuation of its outer width so that the length of the integral nozzle cap 11 may be at least six to eight times more than the outer width.

The other nozzle part is provided as a nozzle core 12 which is arranged totally submerged and firmly seated axially within the nozzle part 11 or the member 9 respectively, e.g. as a press fit. By its end surface areas facing each other the nozzle parts 11, 12 form a guiding means or swirler 13 by means of which the medium is deflected transversely to an axial direction of flow at or between these end surface areas and then caused to flow swirling or rotating about this nozzle axis.

The cap shell 14 of the nozzle 10, simultaneously forming unit tubular shell of the member 9, translates at the free end of the latter integrally into a face end wall 15 which by its inner side forms one of the two cited face end surface areas. Adjoining this face end surface area 16 is the core 12 with its end surface area smooth and flat throughout. Between these end surface areas guide passages are provided which are exclusively formed by groove-like depressions in the face end surface area 16. At the outer circumference of the core 12 an annular passage 17 adjoins as a guiding surface area, from which two transverse or tangential passages 18 emanate evenly distributed about the circumference. Each of these passages 18 merges tangentially in the inner, widest end of a nozzle passage 19 which passes through the face end wall 15 in the nozzle axis starting at the face end surface area 16. The centerline or nozzle axis 21 is located on the centerline of the member 9 and at right angles to the centerline 20 of the head part 8. The nozzle passage 19 is constricted in the direction of the outside of the face end wall 15 and forms in this outer side the nozzle orifice 22 at which the medium is liberated from the head 1 on discharge. This nozzle orifice 22 has a width of less than one or a half millimeter and may be located recessed in the outer side.

The second component of the head 1 is a filler 23 which is linear throughout, rod-shaped and except for a flat 28 axially-symmetrical for the parts 8, 9 and which may be configured at one end integrally with the core 12 or like the latter arranged firmly seated in a mount 24. This mount 24 is defined by the inner circumference 25 of the shell 14 at which the core 12 is positively seated by radial pressure of its outer circumference 26 over the majority of its length or the full length of the member 9.

The outer circumference of the core 12, 23 is provided from the means 13 up to the passage transition to the outlet passage 6 with a single flat 28 extending over an angle of curvature of less than 90 respectively and defining an end passage 27 by the inner circumference 25 having a circular cross-section throughout. This end passage 27, like the passages 17 to 19, has the lesser flow cross-section of the capillary passages, with respect to the passages 17 to 19 a somewhat larger flow cross-section constant throughout its length, as compared to which the largest or smallest flow cross-section of the passage 6 is at least two to three times larger or also at least four times larger.

The rear end of the outlet passage 27 or of the flat 28 adjoins a ring-shaped chamber 29 defined by an inner circumference and an outer circumference, this chamber being formed by a recessed groove partly circular in cross-section in the outer circumference of the filler 23 and the center plane of which lies roughly in an axial plane of the axis 20 of the passage 6. A limited circumferential portion of the chamber 29 is located directly opposite the constricted end surface area of the passage 6 at a slight distance away therefrom so that a passage transition 30 is formed in which the medium flows from the passage 6 radially against the bottom surface area of the chamber 29 and thereinto whilst translating into an annular flow. From the chamber 29 the medium then flows accelerated directly into the rear end of the passage 27. The passage 27 and the core 12, 23 may be located about the axis 21 with respect to the body 7 in any rotary position with the same effect so that automatic assembly of the component 23 is facilitated without the necessity of a rotary orientation.

The head part 8 comprises in the axis 20 an outermost shell 31 and at the end thereof located nearer to the member 9 an outermost face end wall 32, beyond the outer side of which the shell 31 does not protrude. Adjacent to the inner side of the face end wall 32 or provided integrally adjoining thereto a passage housing 33 is provided in the interior of the shell 31, this passage housing extending only over a minor portion of the length of the shell 31, forming an inner continuation of the shell 14 and adjoining the inner circumference of the shell 31 only by its ends. Between these ends the housing 33 is located spaced away at the side from this inner circumference so that it forms a U shape which translates integrally by its legs into the inner side of the face end wall 32.

The housing 33 of the head body 7 comprises in its shell portion facing away from the face end wall 32 a sleeve-shaped connecting member 34 which stands off in the axis 20 from the face end wall 32 freely directed away from the housing 33, is set back with respect to the corresponding open face end surface area of the shell 31 or of the passage 6 and is provided for a firm-seated connection with the counter member 5. The counter member 5 is located as a press-fit and/or snap-seating within the member 34 which is supported by abutment of its end surface area at a transition shoulder between counter member 5 and the remaining plunger 4. The end surface area of the counter member 5 with the outlet opening of the outlet passage 6 is then located approximately in the inner circumference of the passage housing which forms a projection of the mount 24. The member 34 is located roughly in the middle of the length of the passage housing 33.

The medium emerges from the outlet 22 axially in the direction 36, and also the core 12, 23 is inserted in the head body 7 on being assembled in this direction, namely in the assembly direction 37, i.e. transversely or at right angles to the axis 20 and parallel to the axis 21. For this purpose the mount 24 or the housing 33 and the head part 8 in the outermost portion facing away from the member 9 forms an assembly opening 35 which is widened with respect to the mount 24, this assembly opening 35 being closed off following assembly by a closure so tightly that the closure part 39 thereof forms by a face end surface area a barrel-shaped section of the outer circumference of the head part 8. The closure part 39 is defined with respect to the head part 8 by a joint 40 located exclusively within 37 to be jointed together axially which may be a welding, bonding, latching, abutment, press and/or snap fit joint. The hindmost end of the component 23 comprises a head 41 which is widened with respect to the remaining portions thereof which is locked in place at the inner circumference of the housing 33 by a snap-fit joint.

To the front a plurality of axially adjacent claw-type sealing rings 42 adjoins the head 41 which clasp the inner circumference of the housing 33 like sealing lips. The front face end surface area of the head 41 forms a ring-shaped abutment 43 which as a counterstop is spaced away opposite a ring-shaped inner shoulder of the inner circumference of the housing 33. The forwardmost sealing member 42 is located correspondingly opposite a further counterstop 44 so that the outer width of the sealing members 42 is greater than that of the core 23 and smaller than that of the head 41. Directly adjacent to the chamber 29 and adjoining thereto the outer circumference of the core 23 engages via a sealing seat 45 the inner circumference 25 such that the outer circumference of this sealing seat 45 adjoins the inner circumference of the member 34 or protrudes beyond this inner circumference respectively. The medium flowing from the passage 6 into the passage transition 30 is thus able to flow only forwards into the passage 27 and not to the rear through the closure 38. The nozzle 10 may also be configured as a non-atomizing nozzle, e.g. for dispensing droplets or a non-atomized jet. Core 12, 23 includes a tie rod 23 for positionally securing nozzle member 11, 12 against tensile motions with respect to head part 8.

Even if the shell 14 or the face end wall 15 were to fracture the core 12, 23 cannot be expelled in the direction 36. Also, further parts of the member 9, e.g. the shell 14 cannot be expelled in this direction 36, because the core 12, 23 is positively connected to the tubular part 9 via such a great length and surface area that the retaining force cannot be defeated. Apart from this, in the region of its connection 46 the tubular part integrally adjoins the outer circumference of the head part 8, or exclusively the shell 31 or the end of the housing 33 thereof, the same as the face end wall too, so that it is integral throughout therebetween. The outer face end surface area of the face end wall 32 as well as, where necessary, the adjoining portion of the outer circumference of the member 9 forms a scalloped finger grip 47 in the form of a finger-pressure surface for actuating the head 1 with respect to the base body or housing of the discharging device 2 in the direction in which the shell 31 and the member 34 freely protrude.

It will be appreciated that all of the stated properties and effects may be provided for precisely as described, at least partly so or only roughly or substantially so, depending on for which applications the beaker head 1 is provided.

We claim:

1. A discharge head for dispensing media comprising:
  a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20),
  an end duct (27) directly connecting to said media nozzle (10), an outlet duct (6) being provided and directly connecting to said end duct (27) via a duct transition (30), and
  integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8), and
  wherein said end duct (27) is continuously significantly narrower than said outlet duct (6), thereby said end duct (27) throttling flow of the media while flowing from said outlet duct (6) through said duct transition (30) into said end duct (27) and out of said nozzle orifice (22), said nozzle orifice (22) being bounded by an orifice boundary made in one part with said head member (8).

2. The discharge head according to claim 1 and defining passages (30, 29, 27, 17, 18) for guiding the media to said nozzle zone, wherein said head body (7) includes an assembly inlet (35) for inserting said at least one nozzle member (12), said assembly inlet (35) being separate from said passages and penetrating said head body (7) apart from said passages (30, 29, 27, 17, 18), said at least one nozzle member (12) being a nozzle component separate from said head member (8), locking means (40) being included and permanently axially positionally locking said at least one nozzle member (12) with respect to said nozzle orifice (22), said at least one nozzle member (12) being located entirely upstream of said nozzle orifice (22).

3. The discharge head according to claim 2, wherein said at least one nozzle member (11, 12) includes a nozzle core (12) directly connecting to a core rod (23), commonly with said outlet member (9) said core rod (23) bounding said end duct (27), said assembly inlet (35) circumferentially penetrating said head body (7) remote from said nozzle zone at an external head circumference enveloping said actuating axis (20), said core rod (23) including rod faces (28) providing a section of said external head circumference.

4. The discharge head according to claim 2, wherein said head body (7) bounds an internal reception (24) enveloping said least one nozzle member (12) and including a longitudinal boundary (28) of said end duct (27), said assembly inlet (35) being permanently sealingly closed by a closure (38) located adjacent to said duct transition but spaced from said passages and from said nozzle zone, said assembly inlet (35) directly connecting to said end duct (27) in a direction transverse to said actuating axis (20), and around said nozzle axis (21) adjacent to said end duct (27) said nozzle member (12) being press-fitted to said outlet member (9).

5. The discharge head according to claim 1, wherein said outlet member (9) includes a spout for inserting said nozzle zone deeply into a patient's throat and for medically treating the throat by directly applying the media, said spout freely projecting from said head member (8) transverse to said actuating axis (20), said at least one nozzle member (11, 12) including a nozzle sleeve (14) bounding said nozzle orifice (20) and a nozzle core enveloped by said nozzle sleeve (14), said nozzle sleeve (14) and said nozzle core commonly circumferentially bounding said end duct (27) in cross-section, said nozzle core being inserted in said nozzle sleeve (14) in said outlet direction (36), said nozzle sleeve (14) directly connecting to said head member (8) at said transition zone (46).

6. The discharge head according to claim 1, wherein said at least one nozzle member (11, 12) includes separate first and second nozzle members (11, 12) including a nozzle cap (11) and a nozzle core located inside said nozzle cap (11), said first nozzle member (11) being substantially entirely made in one part with said head body (7) and thereby positively locked to said head body (7) against motions in said outlet direction (36), said second nozzle member (12) being positively locked by abutting against at least one counter stop (16, 40, 44) integrally connected to said first nozzle member (11), said outlet member (9) including a spout freely projecting from said head member (8) and including said nozzle cap.

7. The discharge head according to claim 1, wherein said outlet member (9) includes an outlet tube (14) including a rear end and a free end away from said head member (8) for providing said transition zone (46), said rear end being made in one part with said head member (8), said free end including said at least one nozzle member (11, 12) made in one part with said outlet tube (14), said free end including a cap jacket, said cap jacket being integral with said outlet tube.

8. The discharge head according to claim 1, wherein said head member (8) provides an actuating cap including a cap jacket (31) and a cap end wall (32), said actuating cap defining a cap inside and a cap outside remote from said cap inside, said cap outside providing an actuating handle (47) for actuating discharge of the media, entirely inside said actuating cap a duct casing (33) being provided and connecting directly to a portion of said cap inside of said cap end wall (32), said duct casing (33) extending transverse to said actuating axis (20) and including a casing end remote from said outlet member (9), said at least one nozzle member (11, 12) being inserted through said casing end and made integral with said head member (8).

9. The discharge head according to claim 1, wherein said at least one nozzle member (11, 12) includes only two nozzle members (11, 12) including a nozzle cap (11) and a nozzle core located inside said nozzle cap, said nozzle cap (11) being traversed by said nozzle orifice (22), said nozzle cap (11) and said outlet member (9) being made in one part with said head body (7), said nozzle cap (11) radially externally projecting over said head member (8) integral with said head body (7) and including an actuating handle (47) for actuating discharge of the media.

10. The discharge head according to claim 9, wherein said discharge head is assembled from only two separate assembly parts including said head body (7) and said nozzle core (12), said nozzle core including a closure (38) including a seal (42) sealingly closing said assembly inlet (35), said seal (42) including a seal member made in one part with said nozzle core (12) and directly sealingly connecting to said head body (7).

11. The discharge head according to claim 1, wherein a flow twister (13) is provided directly adjacent to said nozzle orifice (22) for swirling the media around said nozzle axis (21), said flow twister (13) including at least one transverse duct (18) directed against said nozzle axis (21), said at least one transverse duct (18) including a duct groove in said outlet member (9) made in one part with said head member (8) and including a tube projection projecting from said head member (8) apart from said actuating axis (20).

12. The discharge head according to claim 1, wherein said at least one nozzle member (11, 12) includes a core body (23) engaging inside said head body (7), said core body (23) being frictionally and positively locked with respect to said head body (7), said core body (23) including a tie rod for positionally securing said at least one nozzle member (11, 12) against tensile motions with respect to said head member (8), said core body (23) being rigidly press-fitted to said head body (7) over substantially an entire length extension of said end duct (27).

13. The discharge head according to claim 1, wherein said at least one nozzle member includes a nozzle component (23) separate from said head body (7), said nozzle component (23) including a nozzle end (12) located at said nozzle zone and a rear end (41) remote from said nozzle zone, a snap fit (40) being included for rigidly connecting said nozzle component (23) to said head body (7).

14. The discharge head according to claim 13, wherein said snap fit (40) is located at said rear end (41) including a snap member.

15. The discharge head according to claim 13, wherein said duct transition (30) is located between said nozzle end (12) and said rear end (41), said rear end (41) including at least one sealing ring (42) radially projecting over said rear end (41), made in one part with said nozzle component (23) and directly sealingly connecting to said head body (7).

16. A discharge head for dispensing media comprising:
a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20),
an end duct (27) directly connecting to said media nozzle (10), an outlet duct (6) being provided and directly connecting to said end duct (27) via a duct transition (30), and
integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8);
wherein said discharge head defines passages (30, 29, 27, 17, 18) for guiding the media to said nozzle zone, wherein said head body (7) includes an assembly inlet (35) for inserting said at least one nozzle member (11, 12), said assembly inlet (35) being separate from said passages and penetrating said head body (7) apart from said passages (30, 29, 27, 17, 18), said at least one nozzle member (12) being a nozzle component separate from said head member (8), locking means (40) being included and permanently axially positionally locking said at least one nozzle member (12) with respect to said nozzle orifice (22), said at least one nozzle member (12) being located entirely upstream of said nozzle orifice (22);
and wherein said discharge head defines a counter direction oriented parallel to and directed counter said outlet direction (36), wherein said at least one nozzle member includes a nozzle body separate from said head body (7), said nozzle body being inserted through said assembly inlet (35) in an assembly direction (37) departing from said counter direction and from parallelism with said actuating axis (20), said nozzle body being inserted against at least one abutment (16, 40, 44) of said locking means for locking said nozzle body with respect to said head member (8), in cross-section transverse to said nozzle axis (21) said nozzle body defining an outer circumference including a partial circumference, said nozzle body bounding said end duct (27) along said partial circumference.

17. The discharge head according to claim 16, wherein said assembly direction (37) is oriented substantially codirectional with said outlet direction (36) and transverse to said actuating axis (20), said nozzle body (12) being circumferentially entirely enveloped by said head body (7).

18. A discharge head for dispensing media comprising:
a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20),
an end duct (27) directly connecting to said media nozzle (10), an outlet duct (6) being provided and directly connecting to said end duct (27) via a duct transition (30), and
integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8);
wherein said discharge head defines passages (30, 29, 27, 17, 18) for guiding the media to said nozzle zone, wherein said head body (7) includes an assembly inlet (35) for inserting said at least one nozzle member (11, 12), said assembly inlet (35) being separate from said passages and penetrating said head body (7) apart from said passages (30, 29, 27, 17, 18), said at least one nozzle member (12) being a nozzle component separate from said head member (8), locking means (40) being included and permanently axially positionally locking said at least one nozzle member (12) with respect to said nozzle orifice (22), said at least one nozzle member (12) being located entirely upstream of said nozzle orifice (22); and wherein said head body (7) bounds an internal reception (24) enveloping said at least one nozzle member (12) and including a longitudinal boundary (28) of said end duct (27), said assembly inlet (35) being permanently sealingly closed by a closure (38) located adjacent to said duct transition but spaced from said passages and from said nozzle zone, said assembly inlet (35) directly connecting to said end duct (27) in a direction transverse to said actuating axis (20), and around said nozzle axis (21) adjacent to said end duct (27) said at least one nozzle member (12) being press-fitted to said outlet member (9); and wherein said outlet duct (6) is oriented transverse to said end duct (27) at least at said duct transition (30), said assembly inlet (35) being eccentric with said end duct (27), while said at least one nozzle member (12) is inserted and passes through said duct transition (30) remote from said nozzle zone, and at a rear end said at least one nozzle member (12) and said closure (38) including a member head (41) wider than an entire remainder of said at least one nozzle member (12), said rear end being entirely countersunk within said head body (7).

19. A discharge head for dispensing media comprising:

a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20), an end duct (27) directly connecting to said media nozzle (10), an outlet duct (6) being provided and directly connecting to said end duct (27) via a duct transition (30), and integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8);

wherein said discharge head defines passages (30, 29, 27, 17, 18) for guiding the media to said nozzle zone, wherein said head body (7) includes an assembly inlet (35) for inserting said at least one nozzle member (11, 12), said assembly inlet (35) being separate from said passages and penetrating said head body (7) apart from said passages (30, 29, 27, 17, 18), said at least one nozzle member (12) being a nozzle component separate from said head member (8), locking means (40) being included and permanently axially positionally locking said at least one nozzle member (12) with respect to said nozzle orifice (22), said at least one nozzle member (12) being located entirely upstream of said nozzle orifice (22); and wherein said head body (7) bounds an internal reception (24) enveloping said least one nozzle member (12) and including a longitudinal boundary (28) of said end duct (27), said assembly inlet (35) being permanently sealingly closed by a closure (38) located adjacent to said duct transition but spaced from said passages and from said nozzle zone, said assembly inlet (35) directly connecting to said end duct (27) in a direction transverse to said actuating axis (20), and around said nozzle axis (21) adjacent to said end duct (27) said at least one nozzle member (12) being press-fitted to said outlet member (9); and wherein said longitudinal boundary (28) is a flat formed on along a portion of a circumference of said at least one nozzle member (12), said flat (28) and said end duct (27) circumferentially only partly extending around said at least one nozzle member (12), said flat (28) extending only over a part of an entire length extension of said at least one nozzle member (12) and transverse to said actuating axis (20).

20. A discharge head for dispensing media comprising:

a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20), an end duct (27) directly connecting to said media nozzle (10), an outlet duct (6) being provided and directly connecting to said end duct (27) via a duct transition (30), and integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8);

wherein said discharge head defines passages (30, 29, 27, 17, 18) for guiding the media to said nozzle zone, wherein said head body (7) includes an assembly inlet (35) for inserting said at least one nozzle member (11, 12), said assembly inlet (35) being separate from said passages and penetrating said head body (7) apart from said passages (30, 29, 27, 17, 18), said at least one nozzle member (12) being a nozzle component separate from said head member (8), locking means (40) being included and permanently axially positionally locking said at least one nozzle member (12) with respect to said nozzle orifice (22), said nozzle member (12) being located entirely upstream of said nozzle orifice (22); and wherein said duct transition (30) directly connects to a distributing chamber (29) bounded by an insert (23), said insert (23) being inserted through said assembly inlet (35), said distributing chamber (29) connecting to said end duct (27) independent from varying rotational positions of said insert (23) with respect to said outlet duct (6), said distributing chamber (29) being bounded by an external circumferential groove of said insert (23).

21. A discharge head for dispensing media comprising:

a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20), an end duct (27) directly connecting to said media nozzle (10), an outlet duct (6) being provided and directly connecting to said end duct (27) via a duct transition (30), and integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8);

wherein said head member (8) provides an actuating cap including a cap jacket (31) and a cap end wall (32), said actuating cap defining a cap inside and a cap outside remote from said cap inside, said cap outside providing an actuating handle (47) for actuating discharge of the media, entirely inside said actuating cap a duct casing (33) being provided and connecting directly to a portion of said cap inside of said cap end wall (32), said duct casing (33) extending transverse to said actuating axis (20) and including a casing end remote from said outlet member (9), said at least one nozzle member (11, 12) being inserted through said casing end and made integral with said head member (8); and wherein said duct casing (33) further includes a front end remote from said casing end, said duct casing (33) directly connecting to said cap inside of said cap jacket (31) substantially only with said casing end and said front end, in cross-section said duct casing (33) freely projecting over said cap inside and being laterally spaced from said cap jacket (31) axially freely projecting over said duct casing (33).

22. A discharge head for dispensing media comprising:

a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20), an end duct (27) directly connecting to said media nozzle (10), an outlet duct (6) being provided and directly connecting to said end duct (27) via a duct transition (30), and integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8);

wherein said head member (8) provides an actuating cap including a cap jacket (31) and a cap end wall (32), said actuating cap defining a cap inside and a cap outside remote from said cap inside, said cap outside providing an actuating handle (47) for actuating discharge of the media, entirely inside said actuating cap a duct casing (33) being provided and connecting directly to a portion of said cap inside of said cap end wall (32), said duct casing (33) extending transverse to said actuating axis (20) and including a casing end remote from said outlet member (9), said at least one nozzle member (11, 12) being inserted through said casing end and made integral with said head member (8); and wherein for connecting said discharge head (1) to an actuating plunger (4) defining said outlet duct (6) said head body (7) includes a connecting member (34) oriented substantially parallel to said actuating axis (20), freely axially projecting from said duct casing (33) and shorter than said cap jacket (31).

23. A discharge head for dispensing media comprising:

a head body (7) including an outlet member (9), a head member (8) and an atomizing nozzle (10), said outlet member (9) defining a nozzle zone in which said atomizing nozzle (10) is located, said atomizing nozzle including at least one nozzle member (11, 12) bounding a nozzle outlet (22), said nozzle outlet defining an outlet direction (36), said head member (8) defining an actuating axis (20) and said atomizing nozzle (10) defining a nozzle axis (21) substantially departing from said actuating axis (20), passages (30, 29, 27, 17, 18) or guiding the media from said outlet duct (6) to said nozzle zone and including an end duct (27) directly connecting to an outlet duct (6) via a duct transition (30), integrating means for integrating said atomizing nozzle (10) with said outlet member (9) and for preventing partial and fractureless release of said at least one nozzle member (11, 12) in said outlet direction (36) while operating said discharge head for dispensing the media under pressure, said head body (7) including an assembly inlet (35) for inserting said at least one nozzle member (11, 12), said assembly inlet (35) being separate from said passages (30, 29, 27, 17, 18) and penetrating said head body (7) apart from said passages (30, 29, 27, 17, 18) for connecting said discharge head (1) to an actuating plunger (4) defining said outlet duct (6) said head body (7) including a connecting member (34) oriented substantially parallel to said actuating axis (20), said connecting member including a tubular connector (34) freely and circumferentially projecting from a duct casing (33) located entirely inside said head member (8), said duct casing (33) bounding said assembly inlet (35), downstream said tubular connector (34) being directed into a distributing chamber (39) annularly distributed substantially in an axial plane of said tubular connector (34) and oriented axially substantially parallel to said end duct (27).

24. A discharge head for dispensing media comprising:

a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20), an end duct (27) directly connecting to said media nozzle (10), an outlet duct (6) being provided and directly connecting to said end duct (27) via a duct transition (30), and integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8), and wherein said head member (8) provides an actuating cap including a cap jacket (31) and a cap end wall (32), said actuating cap defining a cap inside and a cap outside remote from said cap inside, said cap outside providing an actuating handle (47) for actuating discharge of the media, entirely inside said actuating cap a duct casing (33) being provided and connecting directly to a portion of said cap inside of said cap end wall (32), said duct casing (33) extending transverse to said actuating axis (20) and including a casing end remote from said outlet member (9), said at least one nozzle members (11, 12) being inserted through said casing end and made integral with said head member (8).

25. A discharge head for dispensing media comprising:

a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20), an end duct (27) directly connecting to said media nozzle (10), an outlet duct (6) being provided and directly connecting to said end duct (27) via a duct transition (30), and integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8), and wherein said discharge head defines passages (30, 29, 27, 17, 18) for guiding the media to said nozzle zone, wherein said head body (7) includes an assembly inlet (35) for inserting said at least one nozzle member (11, 12), said assembly inlet (35) being separate from said passages and penetrating said head body (7) apart from said passages (30, 29, 27, 17, 18), said at least one nozzle member (12) being a nozzle component separate from said head member (8), locking means (40) being included and permanently axially positionally locking said at least one nozzle member (12) with respect to said nozzle orifice (22), said at least one nozzle member (12) being located entirely upstream of said nozzle orifice (22); and wherein a flow twister (13) is provided directly adjacent to said nozzle orifice (22) for swirling the media around said nozzle axis (21), said flow twister (13) including at least one transverse duct (18) directed against said nozzle axis (21), said at least one transverse duct (18) including a duct groove in said outlet member (9) made in one part with said head member (8) and including a tube projection projecting from said head member (8) apart from said actuating axis (20).

26. A discharge head for dispensing media comprising:

a head body (7) including an outlet member (9), a head member (8) and a media nozzle (10), said outlet member (9) defining a nozzle zone in which said media nozzle (10) is located and defining a transition zone (46) at which said outlet member (9) connects to said head member (8), said media nozzle including at least one nozzle member (11, 12) directly connecting to a nozzle orifice (22), said nozzle orifice defining an outlet direction (36), said head member (8) defining an actuating axis (20) and said media nozzle (10) defining a nozzle axis (21) substantially departing from a direction parallel to said actuating axis (20), an end duct (27) directly connecting to said media nozzle (10), an outlet duct (6) being provided and directly connecting to said end duct (27) via a duct transition (30), and integrating means for integrating said media nozzle (10) with said outlet member (9) and for preventing displacement of said at least one nozzle member (11, 12) in said outlet direction (36), at said transition zone (46) said at least one nozzle member (11, 12) rigidly connecting to said head member (8), and wherein said at least one nozzle member includes a nozzle component (23) separate from said head body (7), said nozzle component (23) including a nozzle end (12) located at said nozzle zone and a rear end (41) remote from said nozzle zone, a snap fit (40) being included for rigidly connecting said nozzle component (23) to said head body (7).

27. The discharge head of claim 26, wherein said snap fit (40) is located at said rear end (41) including a snap member.

* * * * *